(12) United States Patent
Krammer et al.

(10) Patent No.: US 7,635,692 B2
(45) Date of Patent: Dec. 22, 2009

(54) COMPOSITION FOR THE PREVENTION OF OSTEOPOROSIS COMPRISING A COMBINATION OF ISOFLAVONES AND POLYUNSATURATED FATTY ACIDS

(75) Inventors: Stephanie Krammer, Loerrach-Hauingen (DE); Christoph Riegger, Binningen (CH); Manfred Schlachter, Grenzach-Wyhlen (DE); Peter Weber, Malsburg-Marzell (DE)

(73) Assignee: DSM IP Assets B.V., Heerlen (NL)

( * ) Notice: Subject to any disclaimer, the term of this patent is extended or adjusted under 35 U.S.C. 154(b) by 605 days.

(21) Appl. No.: 10/471,890

(22) PCT Filed: Mar. 11, 2002

(86) PCT No.: PCT/EP02/02646

§ 371 (c)(1),
(2), (4) Date: Sep. 11, 2003

(87) PCT Pub. No.: WO02/074308

PCT Pub. Date: Sep. 26, 2002

(65) Prior Publication Data

US 2004/0082523 A1 Apr. 29, 2004

(30) Foreign Application Priority Data

Mar. 15, 2001 (EP) ................................. 01106520

(51) Int. Cl.
*A61K 31/59* (2006.01)
*A61K 31/35* (2006.01)
*A61K 31/20* (2006.01)
*A61K 9/48* (2006.01)
*A61K 9/20* (2006.01)
*A61K 9/14* (2006.01)
*A61K 9/16* (2006.01)
*A01N 45/00* (2006.01)
*A01N 43/16* (2006.01)

(52) U.S. Cl. ........................ 514/167; 424/451; 424/464; 424/489; 424/494; 514/456; 514/558

(58) Field of Classification Search .................. 514/167, 514/456, 558; 424/451, 464, 489, 494
See application file for complete search history.

(56) References Cited

FOREIGN PATENT DOCUMENTS

| EP | 0 517 425 A1 | 12/1992 |
|---|---|---|
| EP | 0 585 026 A1 | 3/1994 |
| WO | WO 96/23504 | 8/1996 |
| WO | WO 99/66913 | * 12/1999 |
| WO | WO 00/00043 | 1/2000 |
| WO | WO 00/69272 | 11/2000 |

OTHER PUBLICATIONS

Treves et al. Clinical rheumatology 1992, 11(4), 558-561.*
Lorenc Calcif Tissue Int 2002, 70, 395-397.*
Ralston The Journal of Clinical Endocrinology & Metabolism 2002, 87(6), 2460-2466.*
Derivative Merriam-Webster's Colegiate Dictionary Tenth Edition Springfield MA 1996, p. 311.*
Rudnic et al. Remington's Pharmaceutical sciences 1990, 18th, 1633-1665.*
Ishimi et al. (Endocrinology 1999, 140(4), 1893-1900).*
Kruger et al. (Prog. Lipid Res. 1997, 36(2/3), 131-151).*
Schaafsma et al. (European journal of Clinical Nutrition 2000, 54, 626-631).*
Horrocks et al. (Pharmacological Research 1999, 40(3), 211 and 219).*
Matsunaga et al. (Calcif Tissue Int 1999, 65, 285-289).*
Patent Abstracts of Japan, vol. 2000, No. 10 of JP 2000191526 (Nov. 17, 2000).
Patent Abstracts of Japan, vol. 1999, No. 4 of JP 11009221 (Apr. 30, 1999).
Patent Abstracts of Japan, vol. 017; No. 037 of JP 04253908 (Jan. 25, 1993).
Weber, "The Role of Vitamins in the Prevention of Osteoporosis—A Brief Status Report," *Int. J. Vitamin. Nutr. Res.*, 69(3), pp. 194-197 (1999).
Khosla, S., Minireview: the OPG/RANKL/RANK system. Endocrinology, 2001. 142(12): p. 5050-5.
Hofbauer, L.C. and A.E. Heufelder, Role of receptor activator of nuclear factor-kappaB ligand and osteoprotegerin in bone cell biology. J Mol Med, 2001. 79(5-6): p. 243-53.
Hofbauer, L.C., et al., Estrogen stimulates gene expression and protein production of osteoprotegerin in human osteoblastic cells. Endocrinology, 1999. 140(9): p. 4367-70.
Hofbauer, L.C., et al., Osteoprotegerin production by human osteoblast lineage cells is stimulated by vitamin D, bone . . . ,Biochem Biophys Res Commun, 1998. 250(3): p. 776-81.
Yamagishi, T., et al., Reciprocal control of expression of mRNAs for osteoclast . . . , Evidence for the involvement of topoisomerase II in osteoclastogenesis, 2001. 142(8): p. 363.
Kruger, M.C. and D.F. Horrobin, Calcium metabolism, osteoporosis and essential fatty acids: a review. Prog Lipid Res, 1997. 36(2-3): p. 131-51.

(Continued)

*Primary Examiner*—Ernst V Arnold
(74) *Attorney, Agent, or Firm*—Bryan Cave LLP

(57) ABSTRACT

A composition, useful in the prevention of osteoporosis, wherein said composition comprises (a) least one isoflavone and/or isoflavone glycoside, preferably genistein and/or genistin; (b) at least one polyunsaturated fatty acid; (c) optionally vitamin D, and /or one or more derivatives thereof and/or vitamin K and/or one or more derivatives thereof; and (d) optionally adjuvants and excipients in quantities as required, preferably within the range of 0.1 to 20% by weight, based on the total weight of the composition. Dietary compositions and galenical forms made therefrom and the use of said compositions for preventing osteoporosis and stimulating osteogenesis in mammals.

17 Claims, No Drawings

OTHER PUBLICATIONS

Ellis, L., et al. Replacement of insulin receptor tyrosine residues 1162 and 1163 compromises insulin-stimulated kinase activity and uptake of . . . , Cell, 1986. 45(5): p. 721-32.

Remington:The Science and Practice of Pharmacy, vol. 1, 19th Ed. 1995, Chapter 41:Drug Absorption, Action and Disposition, section "Drug Interaction and Combination", p. 720-23.

Das, Undurti N., Nitric Oxide as the Mediator of the Antisteoporotic Actions of Estrogen, Statins, and Essential Fatty Acids, Exper. Bio and Med. 227:88-93 (2002).

* cited by examiner

COMPOSITION FOR THE PREVENTION OF OSTEOPOROSIS COMPRISING A COMBINATION OF ISOFLAVONES AND POLYUNSATURATED FATTY ACIDS

This application is the National Stage of International Application No. PCT/EP2002/02646, file Mar. 11, 2002.

The present invention refers to a composition for the prevention of osteoporosis in the form of a concentrate or in the form of a dietary composition such as fortified foods, fortified feed and beverages, or in the form of different galenical formulations such as tablets, granules filled into capsules, or effervescent formulations.

Bone is made mostly of collagen and calcium phosphate. Collagen is the protein that provides a soft framework, and calcium phosphate is the mineral that adds strength and hardens this framework. The combination of collagen and calcium makes the bone strong yet flexible to withstand stress.

Throughout the lifetime, old bone is being resorbed and new bone is being formed. During childhood and teenage years, new bone is added faster than old bone is removed. Beyond the age of about twenty five to thirty years however, bone resorption slowly begins to exceed bone formation, leading to bone loss which ultimately results in osteoporosis.

Bone loss is more pronounced in females than in males. In females bone loss is accelerated during the decade directly following the menopause due to estrogen deficiency but osteoporosis is also age-related to both sexes and is a systemic skeletal disease resulting in low bone mass and micro-architectural deterioration of bone tissue, causing an increase in bone fragility and susceptibility to fracture. The same menopausal situation as described above is seen in female pets, e.g., dogs or cats, following their sterilization, leading to bone loss due to estrogen deficiency.

We have now found that compositions containing an isoflavone in combination with LC-polyunsaturated fatty acids, so called PUFAs, have a significant additive and synergistic effect preventing osteoporosis and stimulating osteogenesis. This effect is further increased if the composition contains vitamin D and vitamin K in defined amounts. The combined intake of genistein, PUFAs and defined amounts of vitamin K and vitamin D surprisingly fully prevents the loss of bone mineral density induced by estrogen deficiency in an OVX-rat model.

Isoflavone is a 3-phenyl-benzo-gamma-pyron. Isoflavones as found in nature generally are substituted by hydroxy or methoxy. The preferred isoflavone within the scope of the present invention is genistein which is 4',5,7-trihydroxy-isoflavone of formula (I)

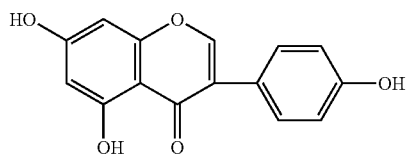

(I)

and which is also found as genistin in the form of its glycoside, for example in soy beans (e.g. Soya hispida). Polyunsaturated fatty acids are known per se (E. A. Trautwein, Eur. J. Lipid Sci. Technol. 103, 2001, p. 45-55).

The present invention is defined in the claims. The present invention specifically refers to a composition, useful in the prevention of osteoporosis, characterized in that said composition comprises:

(a) at least one isoflavone and/or isoflavone glycoside, preferably genistein and/or genistin; and (b) at least one polyunsaturated fatty acid, whereby said composition optionally further comprises (c) vitamin D and/or one or more derivatives thereof and/or vitamin K and/or one or more derivatives thereof, and (d) adjuvants and excipients in quantities as required, preferably within the range of 0.1 to 20% by weight, based on the total weight of the composition.

Said composition may be provided in the form of a concentrate, for example as a simple powdery mixture of its components, or in the form of granules as are obtained for example by spray drying an aqueous slurry of the components or by extruding the mixture, or in the form of tablets as are obtained by compressing the powder into tablets with conventional tabletting methods and machinery, or as pastes filled into hard or soft gelatine capsules, or as effervescent formulations. The present invention further refers to a method of making said composition.

The present invention further refers to the use of said composition in the form of a concentrate for the preparation of a dietary composition or a galenical form, whereby said dietary composition preferably is a fortified food, a fortified feed or a beverage, and said galenical form preferably is a tablet, a granulate or a paste filled into hard or soft gelatine capsules, or an effervescent formulation.

The present invention further refers to a dietary composition, said dietary composition preferably being a fortified food, a fortified feed or a beverage, or to a galenical formulation, said galenical formulation being preferably in the form of a tablet, granules or a paste filled into hard or soft gelatine capsules, or an effervescent formulation, said dietary composition and said galenical formulation each containing the components (a), (b), (c) and (d) as defined above.

The present invention further refers to the use of said composition for preventing osteoporosis and stimulating osteogenesis in mammals, such as, for example humans and pets, including but not limited to cats and dogs.

The present invention further refers to a method of preventing osteoporosis and stimulating osteogenesis in mammals as defined above which comprises administering to a mammal an effective amount of said composition.

Different isoflavones are known, such as daidzein, glycitein, or genistein. Genistein is found as genistin in the form of its glycoside for example in soy beans. According to the present invention the isoflavone itself, or a derivative of isoflavone which yields isoflavone, such as the glycoside, may be used as active component [component (a)] in the composition.

Preferably, the composition contains the isoflavone and/or its derivative in a concentration so that the daily consumption is in the range of from 1 mg to 500 mg, preferably 5 mg to 100 mg.

Polyunsaturated fatty acids (PUFAs) are known per se. Preferred PUFAs are those having from 16 to 24 carbon atoms, preferably from 18 to 22 carbon atoms, more preferably with 18, 20 or 22 carbon atoms and having multiple unsaturated carbon-carbon double bonds.

Examples of such polyunsaturated fatty acids are the known n-3 PUPAs. Preferred are for example PUFAs with 18 carbon atoms such as linoleic acid, e.g. (cic,cis,cis-)9,12,15-octadecatrienoic acid, linolenic acid, e.g. (cic,cis,cis-)6,9,12-octadecatrienoic acid, but also eicosatetranoic acid, eicosapentaenoic acid and docosahexaenoic acid, such as (cis-)5,8,11,14-eicosatetranoic acid, (cis-)5,8,11,14,17-eicosapentaenoic acid and/or (cis-) 4,7,10,13,16,19-docosahexaenoic acid.

Preferably, the composition contains the PUFA in a concentration so that the daily consumption is in the range of from 50 mg to 8000 mg, preferably 500 mg to 2000 mg. Preferably, the composition contains per one milligram of isoflavone or isoflavone derivative [component (a)] about 5 mg to 200 mg, preferably about 20 mg to 50 mg, of polyunsaturated fatty acid [component (b)].

The active metabolite of vitamin D (calcitriol) is known to increase intestinal absorption of calcium and is important for the normal mineralization of new bone. The presence of vitamin D, preferably vitamin $D_3$, improves significantly the effect of the composition according to the present invention. Preferably, the composition contains vitamin D, more preferably vitamin $D_3$, in concentrations known for vitamin D and vitamin $D_3$, respectively. The concentration should be so that a consumption results which is in the range of from 5 µg to 50 µg per day of vitamin D and vitamin $D_3$, respectively.

The classical role of vitamin K is as an antihemorrhagic factor. However, vitamin K also interacts with selected proteins and is a cofactor for these proteins that play a role in bone formation. The presence of vitamin K, preferably vitamin $K_1$, improves the effect of the composition according to the present invention. Preferably, the composition contains vitamin K in concentrations known per se for vitamin K. The concentration of vitamin K and vitamin $K_1$, respectively, should be such that a consumption results which is in the range of 0.050 mg to 10 mg, preferably 0.1 mg to 1.0 mg per day.

As used herein, the terms "vitamin D" refers to both vitamin D and vitamin $D_3$, respectively, as well as to derivatives thereof. The term "vitamin K" refers to both vitamin K and vitamin $K_1$, respectively, and the corresponding derivatives thereof.

Adjuvants may optionally be added. Suitable adjuvants are for example starch, starch derivatives, cellulose, cellulose derivatives (e.g. hydroxypropylmethylcellulose [HPMC], methylcellulose [MC]), and polyol. Preferably, no adjuvants are added to the concentrate.

The composition of this invention may be produced by any known method. The components may be simply mixed together by conventional methods. However, the concentrate is preferably produced in the form of a powder or in the form of granules. Preferred are fluidized-bed granulation, high-shear granulation, extrusion, spray-drying or wet granulation.

For obtaining the composition of the present invention by spraydrying it is convenient to prepare an aqueous slurry of all the components. The slurry has preferably a solid content of about 10% to 70% by weight, more preferably about 25% to 50% by weight. The slurry is then spray-dried in a manner known per se. For obtaining the concentrate of the present invention by fluidized-bed granulation it is convenient to use a known fluidized-bed granulating apparatus which comprises a fluidized-bed drying device fitted with spray means and is operated in a manner known to the skilled person in the art.

The concentrate may further be used in the production of dietary compositions such as a fortified food, a fortified feed or beverages. Such fortified food, fortified feed or beverages are known in the literature and known to the skilled person in the art.

The concentrate may further be compressed into tablets with conventional tabletting methods and machinery. Optionally, the powder or the granules may further be mixed prior to compressing into tablets with a conventional lubricant, including but not limited to metallic stearates, stearic acid, hydrogenated vegetable oils (Sterotex), glyceryl monostearate, glyceryl palmitostearate, talcum, corn starch, polyethylene glycols, sodium benzoate, sodium acetate and sugar esters. A further possibility is mixing the powder or the granules with a mixture of such lubricants and then compressing it into tablets.

Pastes filled into hard or soft gelatine capsules or effervescent formulations are made in conventional manner, whereby these single units contain the same doses as given for tablets.

Experimental Section

In the following experimental section dual-energy X-ray absorptiometry (DXA) was used to measure bone mineral density.

Osteocalcin, a biochemical marker for bone formation, is a bone-specific protein secreted primarily in osteoblasts, i.e. the bone forming cells. Serum osteocalcin was measured as marker for bone formation.

Deoxypyridinoline (DPD) crosslinks excretion provides a highly specific marker for bone resorption. DPD crosslinks excretion was measured as a marker for bone resorption. The values have to be corrected for urinary concentration by creatinine measurement as it is known in the art.

In the experimental set up data were elaborated using the ovariectomized rat osteoporosis (OVX) model. This model mimics the estrogen deficient status as found in postmenopausal women or poststerilized female pets leading to osteoporosis. The SHAM group with intact ovaries served as control. Each test group consisted of 10-12 animals. The feed used was free of isoflavones, such as, for example, genistein. The test compounds in various combinations as given in Table 1 have been administered by feed admix. In rats the genistein dosage of 15 mg/kg BW per day leads to a plasma genistein level comparable to the one found in Japanese people on a traditional diet, i.e. 280 nM. The administration of vitamin $K_1$, in an amount of 20 µg/kg feed corresponds to a daily dosage of about 1 µg/kg BW, the estimated daily requirement of vitamin $K_1$. The amount of vitamin $D_3$ was 500 IU/kg feed which corresponds to a daily dosage of 25 IU/kg BW, the estimated daily requirement. For fortification, PUFA (5% of ROPUPA "30" n-3 Food Oil) was added to the feed corresponding to a PUPA fortification of % in feed as given in Table 1. Bone mineral density, osteocalcin, and deoxypyridinolin have been measured 84 days post intervention.

TABLE 1

Experimental groups and concentration of test compounds in feed

| Group No. | SHAM/ OVX | Feed description | Genistein mg/kg BW | n-3 PUFA % feed | Vitamin $K_1$ µg/kg feed | Vitamin $D_3$ IU/kg feed |
|---|---|---|---|---|---|---|
| 1 | SHAM | Vit. K + D suppl. | | | 2000 | 1500 |
| 2 | OVX | Vit. K + D Suppl. | | | 2000 | 1500 |
| 3 | OVX | | | | 20 | 500 |
| 4 | OVX | n-3 PUFA | | 5 | 20 | 500 |
| 5 | OVX | Genistein | 15 | | 20 | 500 |
| 6 | OVX | Vit. K + D suppl. n-3 PUFA Genistein | 15 | 5 | 2000 | 1500 |

SHAM: intact ovaries model (as a control)
OVX: ovariectomized rat osteoporosis model
BW: body weight
Genistein: Roche No. 24-2076, Roche Vitamins AG, Basel, Switzerland
PUFA: ROPUFA "30" n-3 Food Oil, Roche Vitamins AG, Basel, Switzerland Bone mineral density (BMD) measurement in the femur of OVX rats:

Compared to the SHAM operated animals of group 1, the ovariectomized animals of group 2 and 3 on either a high or low vitamin K and D diet showed a significant decrease in BMD as expected. Group 2 on high vitamin K and D feed did not preserve BMD significantly better than group 3 animals on a low vitamin K and D feed.

The animals of group 4 on a low vitamin K and D feed supplemented with PUFA showed significant preservation of BMD compared to group 3 on a low vitamin K and D feed. However, this group performed not significantly better than group 2 on a high vitamin K and D feed without PUFA supplementation. At the same time BMD of group 4 was not significantly different from the one of the SHAM operated animals. The same result was obtained with group 5 on a low vitamin K and D feed supplemented with genistein. Group 6 on a high vitamin K and D feed supplemented with PUFA and genistein in combination showed a significantly improved BMD compared to group 2 and 3. No significant difference in BMD was found compared to the control group 1. Results are given in Table 2. Supplementation of n-3 PUPA or genistein improved BMD to control values but did not significantly exceed the effect of vitamin D and vitamin K supplementation. Supplementation of vitamin K and D in combination with n-3 PUFA and genistein resulted in the greatest regain of BMD which significantly exceeded the effect of vitamin D and K supplementation and even slightly exceeded the BMD in the SHAM-operated control animals.

TABLE 2

Bone mineral density of femur at day 84 postintervention

| Group No. | SHAM/ OVX | Feed description | Mean g/cm² | Standard Deviation | Significant difference(*) |
|---|---|---|---|---|---|
| 1 | SHAM | Vit. K + D suppl. | 0.143 | 0.006 | a |
| 2 | OVX | Vit. K + D suppl. | 0.135 | 0.012 | bc |
| 3 | OVX | | 0.133 | 0.004 | b |
| 4 | OVX | n-3 PUFA | 0.142 | 0.011 | ac |
| 5 | OVX | Genistein | 0.143 | 0.013 | ac |
| 6 | OVX | Vit. K + D suppl. n-3 PUFA Genistein | 0.145 | 0.011 | a |

(*)Different letters indicate significant differences (p < 0.05) between groups.

Serum Osteocalcin (bone formation marker) measurement in OVX rats:

Estrogen deficiency results in an increased bone turnover resulting in higher levels of serum osteocalcin. Compared to the control group, group 2 and 3 exhibited significantly increased osteocalcin levels, whereas the one of group 3 that was on a low vitamin K and D feed was again significantly higher than the one of group 2 on a high vitamin D and K level. Supplementation of n-3 PUFA or genistein on top of a low vitamin K and D level, group 4 and 5, reduced osteocalcin levels to control values. There was no significant difference in effect between n-3 PUFA and genistein. Group 6 on a feed high in vitamin K and D containing n-3 PUFA and genistein showed the best results, i.e. best effects on osteocalcin levels, and was significantly better than group 4. Results are given in Table 3.

TABLE 3

Serum osteocalcin serum concentration at day 84 postintervention

| Group No. | SHAM/ OVX | Feed description | Mean serum conc. ng/ml | Standard Deviation | Significant difference(*) |
|---|---|---|---|---|---|
| 1 | SHAM | Vit. K + D suppl. | 15.5 | 2.7 | bd |
| 2 | OVX | Vit. K + D | 28.4 | 4.8 | c |
| 3 | OVX | suppl. | 39.6 | 4.9 | a |
| 4 | OVX | n-3 PUFA | 17.8 | 2.9 | d |
| 5 | OVX | Genistein | 14.6 | 3.8 | bd |
| 6 | OVX | Vit. K + D suppl. n-3 PUFA Genistein | 12.8 | 3.6 | b |

(*)Different letters indicate significant differences (p < 0.05) between groups.

Deoxypyridinoline (bone resorption marker) measurement in OVX rats:

Estrogen deficiency resulted in a significant increase of deoxypyridinoline (DPD) excretion which is significantly higher in the group on a low vitamin K and D feed compared to the one on a feed with high vitamin K and D content. The effect of n-3 PUFA supplementation is comparable to the one of a high vitamin K and D feed. The genistein containing feed with low vitamin K and D levels (group 5) restores DPD excretion to values of the control group. Group 6 did not exhibit significant further improvement compared to group 5. Results are given in Table 4, showing that among the compounds tested genistein is the most effective one in restoring control DPD excretion values (group 5), whereas addition of n-3 PUFAs to the feed (group 4) did not exceed the effect obtained by a high vitamin K and D diet (group 2).

TABLE 4

Deoxypyridinoline excretion at day 84 postintervention

| Group No. | SHAM/ OVX | Feed description | Mean nmol DPD/ mmol Creatinine | Standard Deviation | Significant difference(*) |
|---|---|---|---|---|---|
| 1 | SHAM | Vit. K + D suppl. | 210.3 | 19.1 | b |
| 2 | OVX | Vit. K + D | 281.6 | 27.9 | cd |
| 3 | OVX | suppl. | 339.6 | 25.4 | a |
| 4 | OVX | n-3 PUFA | 265.8 | 17.5 | d |
| 5 | OVX | Genistein | 220.5 | 23.5 | b |
| 6 | OVX | Vit. K + D suppl. n-3 PUFA Genistein | 214.3 | 33.3 | b |

(*)Different letters indicate significant differences (p < 0.05) between groups.

From the experimental data shown above one can conclude that the combined intake of genistein, n-3 PUFAs and high amounts of vitamin K and D surprisingly fully prevents the loss of bone mineral density induced by estrogen deficiency.

The invention claimed is:

1. A composition useful for the treatment of osteoporosis consisting of a mixture of the following components:
   (a) genistein, genistin, or a mixture thereof;
   (b) a docosahexaenoic acid (DHA); and
   (c) optionally a vitamin which is selected from the group consisting of vitamin D, vitamin $D_3$, vitamin K, vitamin $K_1$, and mixtures thereof.

2. The composition according to claim 1, wherein the DHA is (cis-)4,7,10,13,16,19-docosahexaenic acid.

3. The composition according to claim 2, wherein said composition is provided in a form selected from the group consisting of concentrates, granules, tablets, pastes filled into hard or soft gelatine capsules, and effervescent formulations.

4. A dietary composition in the form of a fortified feed or a beverage, comprising a composition according to claim 2.

5. A galenical formulation in the form of tablets, granules, pastes filled into hard or soft gelatine capsules, or effervescent formulations, comprising a composition according to claim 2.

6. The composition according to claim 1, wherein the DHA is in an amount of from 50 mg to 8000 mg.

7. The composition according to claim 6, wherein the DHA is in an amount in the range of from 500 mg to 2000 mg.

8. The composition according to claim 1, wherein about 5 to 200 mg of DHA is present per mg of component (a).

9. The composition according to claim 1, wherein the amount of each of vitamin D and vitamin $D_3$ is in the range of from 5 µg to 50 µg, and the amount of each of vitamin K and vitamin $K_1$ is in the range of from 0.050 mg to 10 mg.

10. The composition according to claim 1 wherein, said composition is provided in a form selected from the group consisting of concentrates, granules, tablets, pastes filled into hard or soft gelatine capsules, and effervescent formulations.

11. The composition of claim 10 in the form of a concentrate which is a simple powdery mixture of its components.

12. The composition in the form of granules according to claim 10 obtainable by fluidized-bed granulation, high-shear granulation, extrusion, spray-drying or wet granulation.

13. A dietary composition in the form of a fortified feed or a beverage, comprising a composition according to claim 1.

14. A galenical formulation in the form of tablets, granules, pastes filled into hard or soft gelatine capsules, or effervescent formulations, comprising a composition according to claim 1.

15. A composition for use in the treatment of osteoporosis and for osteogenesis in mammals, said composition comprising the following components:
 (a) genistein in the range of from 5 to 100 mg;
 (b) a docosahexaenoic acid (DHA);
 (c) a vitamin which is selected from the group consisting of vitamin D, vitamin $D_3$, and mixtures thereof in the range of from 5 µg to 50 µg;
 (d) a vitamin which is selected from the group consisting of vitamin K, vitamin $K_1$, and mixtures thereof in the range of from 0.050 mg to 10 mg; and
 (e) optionally adjuvants and or excipients.

16. The composition according to claim 15 wherein about 5 to 200 mg of DHA is present per mg of genistein.

17. The composition according to claim 15 wherein adjuvants and or excipients are present from 0.1 to 20% by weight, based on the total weight of the composition.

* * * * *

UNITED STATES PATENT AND TRADEMARK OFFICE
CERTIFICATE OF CORRECTION

PATENT NO.        : 7,635,692 B2
APPLICATION NO.   : 10/471890
DATED             : December 22, 2009
INVENTOR(S)       : Krammer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1035 days.

Signed and Sealed this

Ninth Day of November, 2010

David J. Kappos
*Director of the United States Patent and Trademark Office*